(12) United States Patent
Cao et al.

(10) Patent No.: US 7,829,852 B2
(45) Date of Patent: Nov. 9, 2010

(54) DEVICE HAVING ETCHED FEATURE WITH SHRINKAGE CARRYOVER

(75) Inventors: Gary X. Cao, Santa Clara, CA (US);
George Chen, Los Gatos, CA (US);
Brandon L. Ward, San Jose, CA (US);
Nancy J. Wheeler, Mountain View, CA (US); Alan Wong, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 620 days.

(21) Appl. No.: 11/864,761

(22) Filed: Sep. 28, 2007

(65) Prior Publication Data

US 2008/0020302 A1    Jan. 24, 2008

Related U.S. Application Data

(62) Division of application No. 10/886,387, filed on Jul. 7, 2004, now Pat. No. 7,285,781.

(51) Int. Cl.
*G01N 23/00* (2006.01)
*G01B 11/02* (2006.01)
*H01L 21/00* (2006.01)
*H01L 21/306* (2006.01)
*C09K 13/00* (2006.01)

(52) U.S. Cl. ............. 250/306; 250/49.22; 250/492.3; 356/635; 356/636; 438/8; 252/79.1; 156/345.15; 156/345.24

(58) Field of Classification Search ............ 250/306, 250/307, 309–311, 461.1, 504 R, 458.1, 459.1, 250/492.1, 492.2, 492.3; 430/30, 269, 296, 430/299, 302, 310–314, 317, 318, 322, 323, 430/325, 326, 328, 330, 331, 394, 396; 356/630, 356/634–636; 438/8, 16, 584, 689, 690, 438/717, 734, 745; 252/79.1, 79.4; 355/27, 355/40, 67; 101/483, 484; 156/345.1, 345.11, 156/345.15, 345.24, 345.31
See application file for complete search history.

(56) References Cited

U.S. PATENT DOCUMENTS 5,654,811 A * 8/1997 Spitzer et al. ............... 349/106

(Continued)

*Primary Examiner*—Bernard E Souw
(74) *Attorney, Agent, or Firm*—Blakely, Sokoloff, Taylor & Zafman LLP

(57) ABSTRACT

In an embodiment of the present invention, a device includes a first etched feature located in a critical dimension scanning electron microscope (CD-SEM) characterization location, the first etched feature having an upper section, a middle section, and a lower section wherein the middle section is severely shrunk relative to a corresponding middle section of a second etched feature having similar dimensions and composition that is not located in a CD-SEM characterization location. In another embodiment of the present invention, the middle section of the first etched feature has a shrinkage carryover exceeding a threshold. In still another embodiment of the present invention, the middle section of the first etched feature exhibits a line edge roughness.

20 Claims, 7 Drawing Sheets

U.S. PATENT DOCUMENTS

| | | | |
|---|---|---|---|
| 5,661,371 A * | 8/1997 | Salerno et al. | 315/169.3 |
| 6,319,655 B1 | 11/2001 | Wong et al. | |
| 6,541,182 B1 | 4/2003 | Dogue et al. | |
| 6,730,458 B1 | 5/2004 | Kim et al. | |
| 6,753,129 B2 | 6/2004 | Livesay et al. | |
| 6,774,044 B2 | 8/2004 | Ke et al. | |
| 6,776,094 B1 * | 8/2004 | Whitesides et al. | 101/327 |
| 6,833,221 B2 | 12/2004 | McArthur et al. | |
| 7,064,846 B1 | 6/2006 | Amblard et al. | |
| 7,195,733 B2 * | 3/2007 | Rogers et al. | 264/496 |
| 7,285,781 B2 * | 10/2007 | Cao et al. | 250/311 |
| 7,666,578 B2 * | 2/2010 | Fischer et al. | 430/314 |
| 2003/0022072 A1 | 1/2003 | Campi et al. | |
| 2003/0224252 A1 | 12/2003 | Zhou et al. | |
| 2004/0152024 A1 | 8/2004 | Livesay et al. | |
| 2005/0023463 A1 | 2/2005 | Ke et al. | |
| 2006/0006328 A1 * | 1/2006 | Cao et al. | 250/310 |
| 2006/0154181 A1 | 7/2006 | Hada et al. | |
| 2007/0281219 A1 * | 12/2007 | Sandhu | 430/5 |
| 2009/0042389 A1 * | 2/2009 | Ho | 438/689 |

* cited by examiner

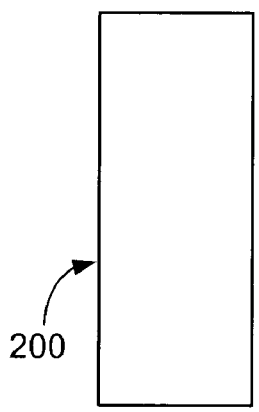
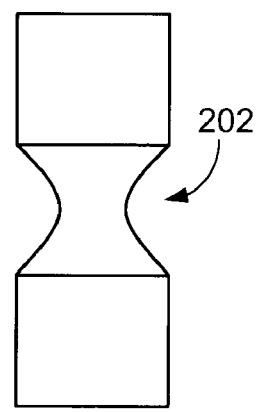
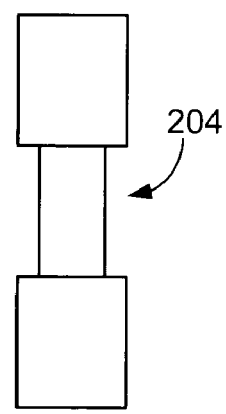
FIG. 2A　　FIG. 2B　　FIG. 2C
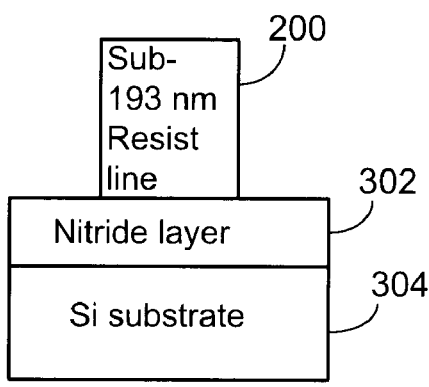
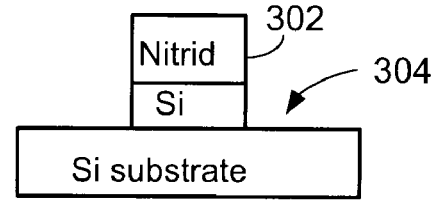
FIG. 3A　　　　　　　FIG. 3B
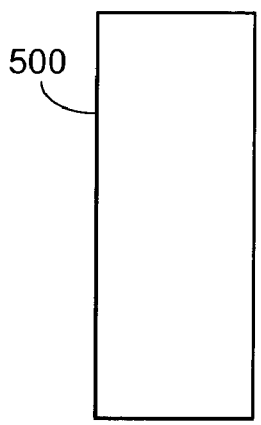
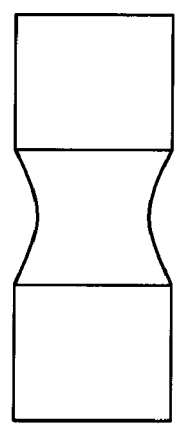
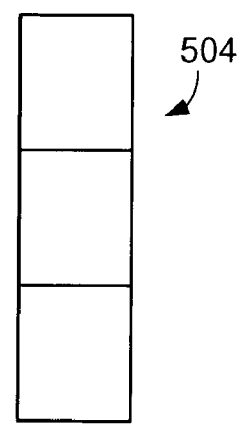
FIG. 5A　　FIG. 5B　　FIG. 5C ial of patent application Ser.
DEVICE HAVING ETCHED FEATURE WITH SHRINKAGE CARRYOVER

CROSS-REFERENCE TO RELATED APPLICATIONS

This application is a divisional of patent application Ser. No. 10/886,387, filed on Jul. 7, 2004, now U.S. Pat. No. 7,285,781 entitled "CHARACTERIZING RESIST LINE SHRINKAGE DUE TO CD-SEM INSPECTION".

BACKGROUND

Scanning Electron Microscopes (SEMs) may be used by semiconductor device manufacturers to measure the "critical dimension" (CD) of the sub-micron-sized circuits in a chip in order to monitor the accuracy of their manufacturing process. CD measurements are typically performed after photolithographic patterning and subsequent etch processing.

An SEM uses a beam of electrons which is shaped and focused by magnetic and electrostatic "lenses" within an electron column. This beam causes secondary electrons and backscattered electrons to be released from the wafer surface. The SEM may then analyze the collected electrons (mainly the secondary electrons) to extract information, e.g., an image or measurement. The use of extremely precise and narrow electron beams may enable SEMs to image and measure features on a semiconductor wafer at a much higher resolution than images captured by optical microscopes.

BRIEF DESCRIPTION OF THE DRAWINGS

FIG. 2A is a plan view of a resist line before a CD-SEM measurement at an initial condition.

FIG. 2B is a plan view of the resist line of FIG. 2A after a CD-SEM measurement at the initial condition.

FIG. 2C is a plan view of a line in the substrate after etching the resist line of FIG. 2B.

FIG. 3A is a sectional view of the resist line of FIG. 2A.

FIG. 3B is a sectional view of the feature line of FIG. 2C.

FIG. 5A is a plan view of a resist line before a CD-SEM measurement at a modified condition.

FIG. 5B is a plan view of the resist line of FIG. 5A after a CD-SEM measurement at the modified condition.

FIG. 5C is a plan view of a line in the substrate after etching the resist line of FIG. 5B.

DETAILED DESCRIPTION

Figure 1:
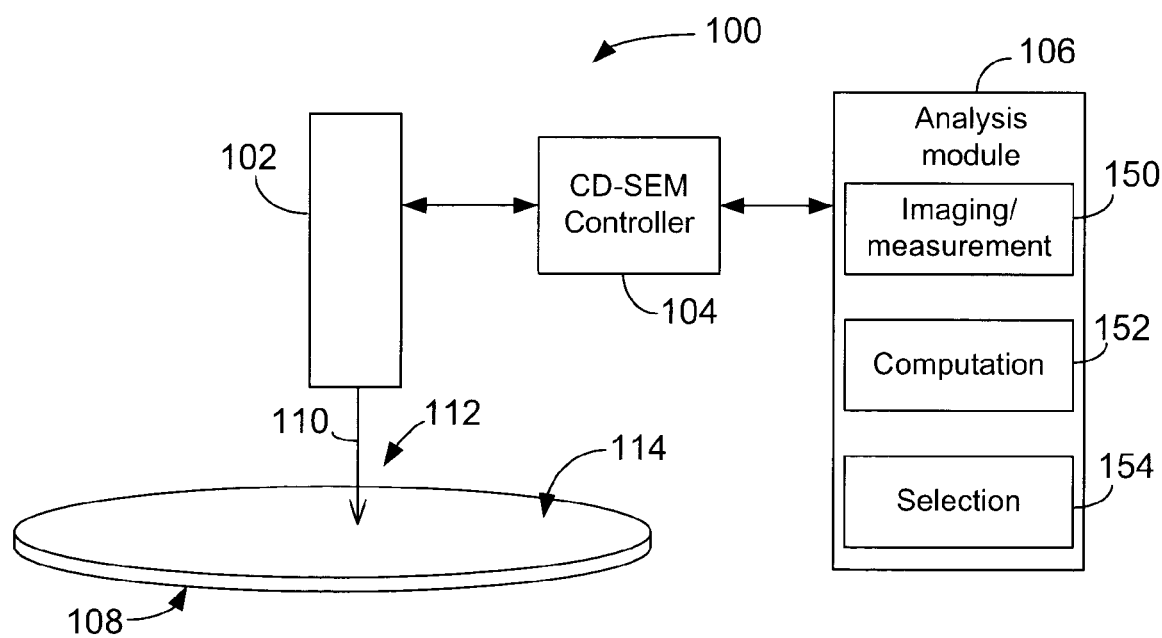
FIG. 1 is a block diagram of a CD-SEM (Critical Dimension-Scanning Electron Microscope) system.

FIG. 1 shows a CD-SEM (Critical Dimension-Scanning Electron Microscope) system 100 according to an embodiment. The system may include a CD-SEM 102, a CD-SEM controller 104 to control the operation and operating parameters of the CD-SEM 102, and an analysis module 106 to analyze the data collected by the CD-SEM.

The CD-SEM system 100 may be used to measure the CD of features in devices on a wafer 108 in order to monitor the accuracy of the manufacturing process. The CD measurements may be performed after photolithographic patterning and subsequent etch processing, e.g., on the patterned resist layer prior to etching the substrate and also on the etched layer.

The CD-SEM 102 produces a beam 110 of electrons, which is shaped and focused by magnetic and electrostatic "lenses" within an electron column. The beam causes secondary electrons and backscattered electrons 112 to be released from the wafer surface 114, which may be collected by the CD-SEM. The analysis module 106 may include an imaging/measurement module 150 to generate an image or measurement from information obtained from the collected secondary electrons.

The photoresist material used in a lithography process may be specific to the wavelength of light used in the lithography system. For example, 193 nm resist materials may be used in a lithography system using 193 nm UV light to expose the mask pattern onto the wafer. Next generation lithography system may use sub-193 nm wavelengths, e.g., 126 nm and 157 nm wavelengths generated by argon excimer and fluorine lasers, respectively. The sensitivity of these resist materials may be such that they are affected by the CD-SEM electron beam 110 used to measure features in the patterned photoresist layer.

FIGS. 2A-2C show the affect of the CD-SEM measurement on a line 200 of 193 nm resist. FIG. 2A shows the line before the measurement by the CD-SEM 102. FIG. 2B shows that the middle of the line 202 is severely shrunk after measurement with the CD-SEM. This shrinkage may be, a physical effect such as a thermal effect, a chemical effect involving changes in bond structure and atomic group re-arrangement, or a combination of both. Because the line shrinkage occurs during measurement, determining the true CD line value from the obtained CD-SEM measurement may be extremely difficult.

FIG. 3A is a sectional view showing the resist line 200 prior to etching. During etching, the photoresist is removed, and the nitride layer 302 and a portion of the substrate 304 may be etched, thereby transferring the pattern in the photoresist layer to the semiconductor device layers (e.g., nitride and silicon substrate). FIG. 2C shows the result of the shrinkage in the photoresist line due to the CD-SEM measurement after etching. The shrunk section 202 in the resist line 200 may result in a thinned portion 204 in the etched line in the device layers. While CD measurements may typically be performed in the scribe line between die (non-device) regions on the wafer, in some cases, it may be necessary to perform CD measurements in the device. The shrinkage carryover, or "fingerprint", from the CD-SEM measurement of the resist line may affect the performance of the device. Thus, CD-SEM measurements may not only be inaccurate, they may adversely affect yield.

In an embodiment, the affects of CD-SEM measurements on the resist may be identified, and the operating parameters adjusted for a particular resist to avoid or significantly reduce shrinkage carryover in order to obtain more reliable CD measurements and avoid damage to the measured feature.

Figure 4:
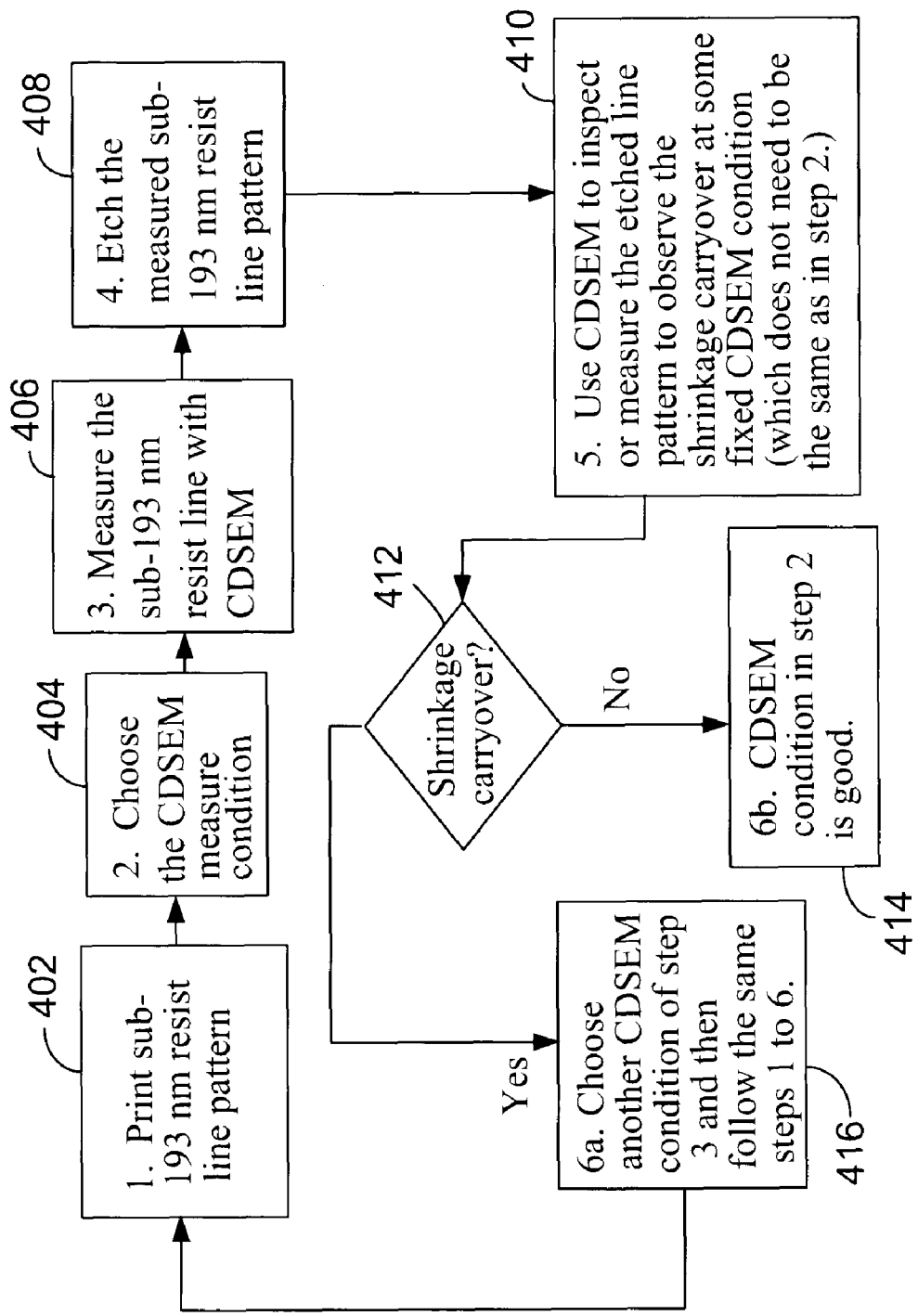
FIG. 4 is a flowchart describing a technique for characterizing and reducing shrinkage carryover due to CD-SEM measurements.

FIG. 4 is a flowchart describing a technique for characterizing and reducing shrinkage carryover due to CD-SEM measurements. A resist line pattern may be printed on the wafer (block 402). A CD-SEM condition may then be selected (block 404). The condition may be a set of operating parameters. The operating parameters for a CD-SEM measurement may include, for example, beam voltage, probe current, dose of electron energy, focusing method, image scanning frames, etc. A resist line in the pattern may then be measured with the electron beam with the selected parameters (block 406). The measured resist line (and the rest of the patterned resist layer) may be etched to produce features in the wafer (block 408). The CD-SEM may then be used again to measure the etched line pattern to observe any shrinkage carryover at some fixed CD-SEM condition (block 410). Measurements may be taken of the measured location and an unmeasured location. The shrinkage carryover may be calculated by a computation module 152 from the two measurements. Also, the shrinkage carryover may manifest itself as a slimming of a resist line, or conversely, enlargement of negative feature, such as a hole (e.g., via) or space, by slimming of the resist edges surrounding the negative feature.

The CD-SEM condition for the second measurement may not necessarily have to be the same as that in block 406 because the etched feature in the device layers may not be as susceptible to damage as the photoresist material. Consequently, the second measurement may be more accurate and non-damaging. The results of the measurement may then be analyzed by the analysis module 106 for evidence of shrinkage carryover (block 412). If no shrinkage carryover is discovered (or it falls below a threshold) (block 414), the condition used to measure in block 406 may be deemed satisfactory for the particular resist material under testing. This condition is shown in FIGS. 5A-5C, where the unshrunk resist line 500 (FIG. 5A) is lightly shrunk 502 after CD measurement (FIG. 5B) and then etched, resulting in a line 504 with no (or below threshold) shrinkage carryover (FIG. 5C). However, if shrinkage carryover (over a certain threshold) is observed (block 416), a new condition may be selected by a selection module 154 in the analysis module 106. The threshold may be based on an amount of shrinkage that is tolerable without causing device failure or malfunction, and in terms of change in width (CD) this may be about 1% of the feature size, depending on the processes and technologies. For example, a width change of 1/10 (or 10 nm) for a feature size of 100 nm may be unacceptable, whereas a width change of 1/50 (or 2% or 2 nm) of the feature size of 100 nm may be acceptable. On the other hand, for a larger feature size of 1000 nm, the shrinkage carryover may not tolerate a threshold value as small as 2% which is 20 nm. Thus the threshold may be selected based on the line (feature) dimension (CD) range. This is because shrinkage carryover may not be a linear function of feature size. For example, for a CD range of 100-200 nm features, the shrinkage carryover amount may be between 10% and 15%, corresponding to values of 10 nm to 30 nm. However, for larger CDs, e.g., in the 1000 nm (1.0 micron) range, a 30 nm shrinkage carryover is a much smaller value in percentage, e.g., about 3%.

Another resist layer may be printed and blocks 404-412 repeated with new CD-SEM condition(s) until a satisfactory CD-SEM condition is determined for the resist material under consideration.

Figure 6:
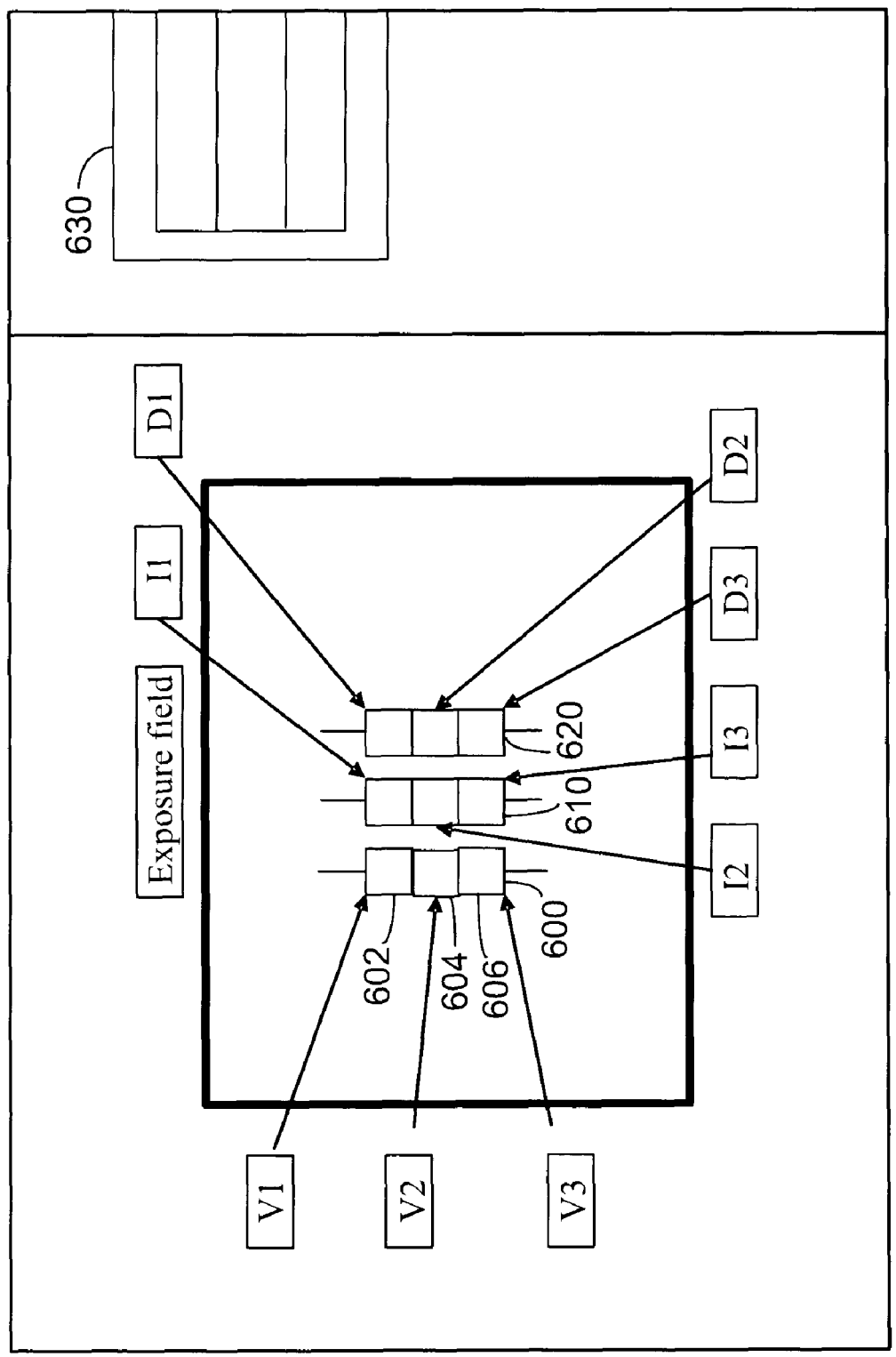
FIG. 6 is a plan view of a test region on a wafer according to an embodiment.

In an embodiment, a technique for characterizing and reducing shrinkage carryover due to CD-SEM measurements may include performing multiple measurements using varying CD-SEM conditions, e.g., voltage, probe current, and dose, on different parts of the same feature, as shown in FIG. 6. For example, the measurement at the upper portion 602 of a line feature 600 may be taken at a voltage V1, a mid portion 604 at a voltage V2, and a lower portion 606 at a voltage V3 (e.g., where V1<V2<V3), while maintaining the probe current at a current I1 for all three measurements. The three portions of the line feature may be completely separated or may have considerable overlaps. The resist shrinkage carryover may then be characterized as a function of beam voltage. Similarly, multiple measurements using varying probe currents (e.g., I1<I2<I3) may be performed on different portions of another line feature 610. Another set of measurements may be taken at varying dose of electron energy (e.g., D1<D2<D3) of another line feature 620. The three sets of measurements mentioned above can be performed on the same type of feature, such as a line, within the same exposure field.

Figure 7:
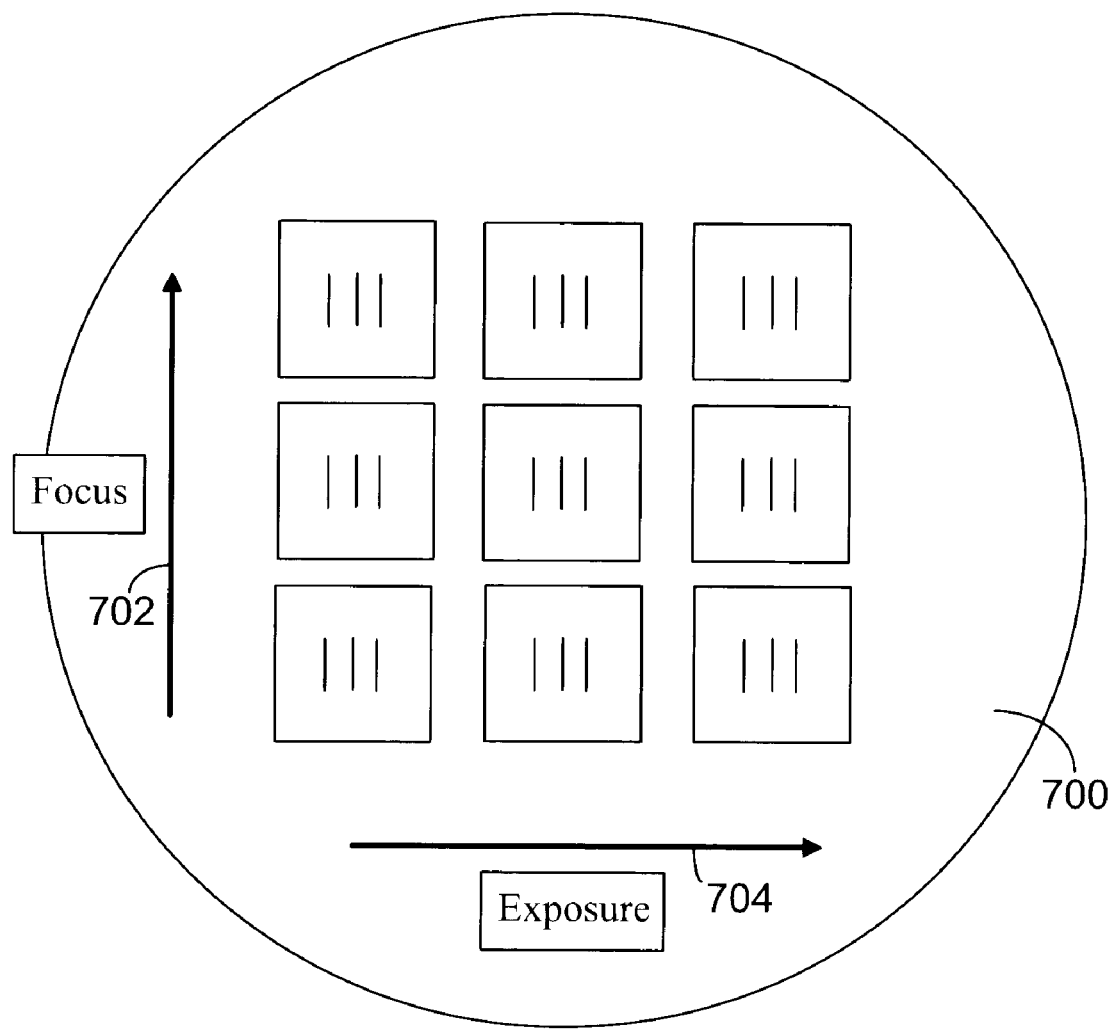
FIG. 7 is a plan view of a test region on a wafer according to another embodiment.

In an embodiment, measurements may be performed in a matrix of lithographic conditions, e.g., focus 702 and exposure 704, on a wafer 700, as shown in FIG. 7. The resist features may be printed under a range of focus and exposure settings, causing the resist profile to vary among the features in different fields. A characterization technique may be repeated in each field of interest for the characterization of the resist shrinkage carryover among different lithographic conditions.

The test features shown in FIGS. 6 and 7 may be provided in a scribe line of the wafer, or in the actual chips in unused regions 625 of one or more device layers. The features may be structurally similar to actual features in the chip (e.g., circuit components 630), but non-functional.

In an embodiment, substantially identical test features may be used to test and compare different CD-SEM tools. The amount of shrinkage carryover caused by the different CD-SEM tools at the same conditions may be compared for selection of a CD-SEM tool for a particular implementation.

Figure 8A:
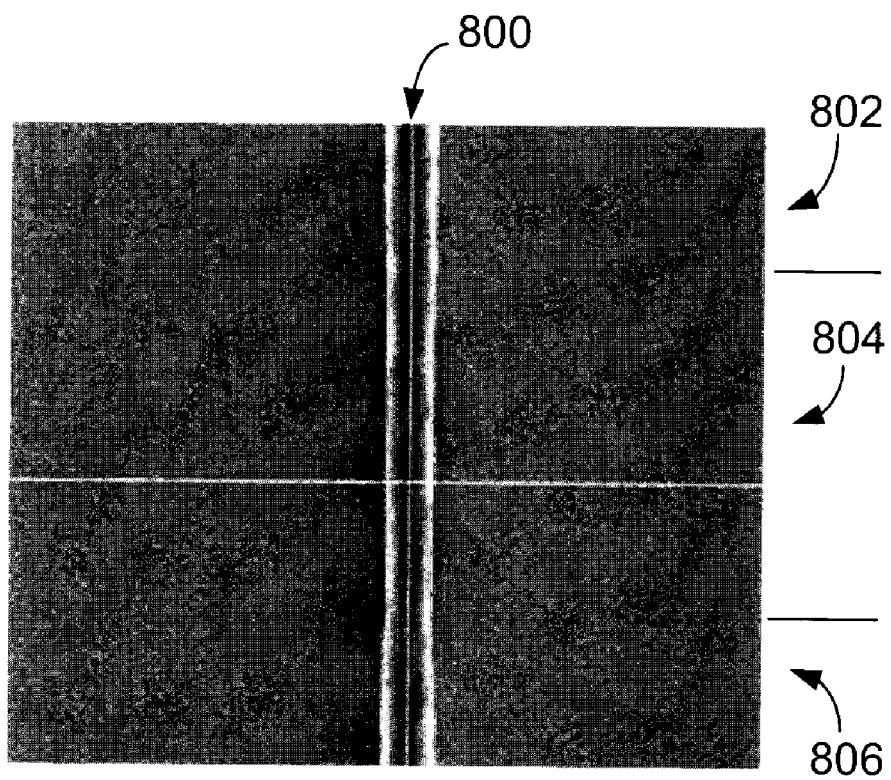
FIG. 8A is an image of a resist line having severe shrinkage or slimming effect due to CD-SEM measurement.

FIG. 8A shows shrinkage in a P8×5 193 nm resist line 800 due to measurement with an 800V CD-SEM beam voltage condition. The line includes an upper section 802, a middle section 804, and a lower section 806. A measurement in the middle section 804 causes the line to shrink by over 10% in the middle section 804. This corresponds to the slimming of the middle section 202 of the resist line shown in FIG. 2B.

Figure 8B:
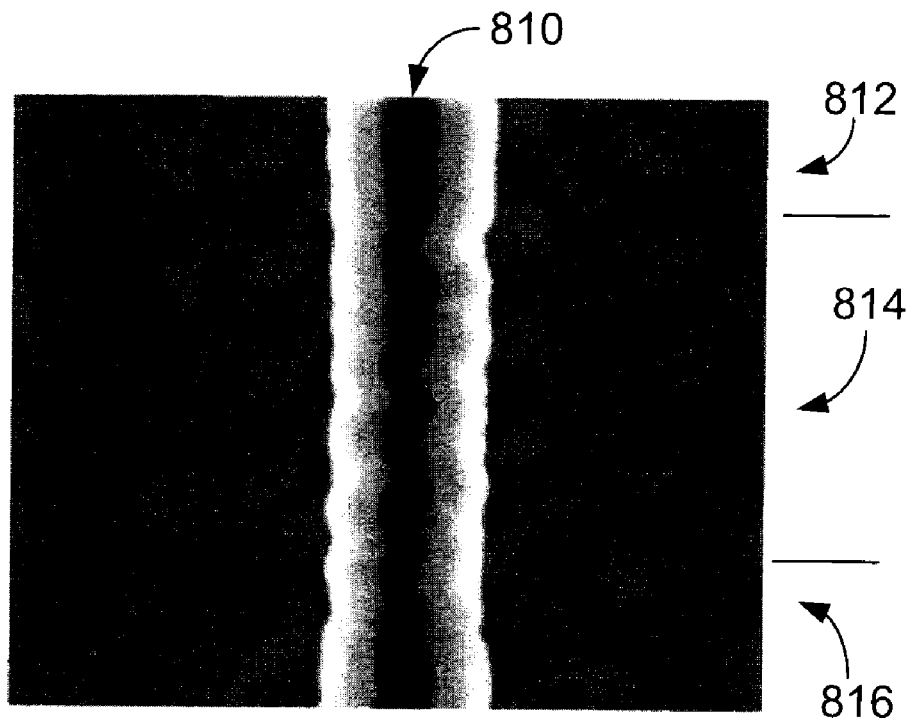
FIG. 8B is an image of a post-etch line pattern showing shrinkage carryover or fingerprint corresponding the shrunk resist line of FIG. 8A.

FIG. 8B shows the corresponding post-etch shrinkage fingerprint (i.e., shrinkage carryover) in the etched line 810, with upper section 812, middle section 814, and lower section 816. The magnitude of shrinkage carryover in the middle section 814 of the etched line in this case is greater than 15% compared with an unmeasured line. This corresponds to the thinned middle portion 204 of the etched line shown in FIG. 2C. The middle section 814 of the etched line in this case also exhibits line edge roughness, which may also be induced by an SEM measurement in the resist measurement step. Consequently, line edge roughness effects may also be reduced using the techniques described above.

Figure 9:
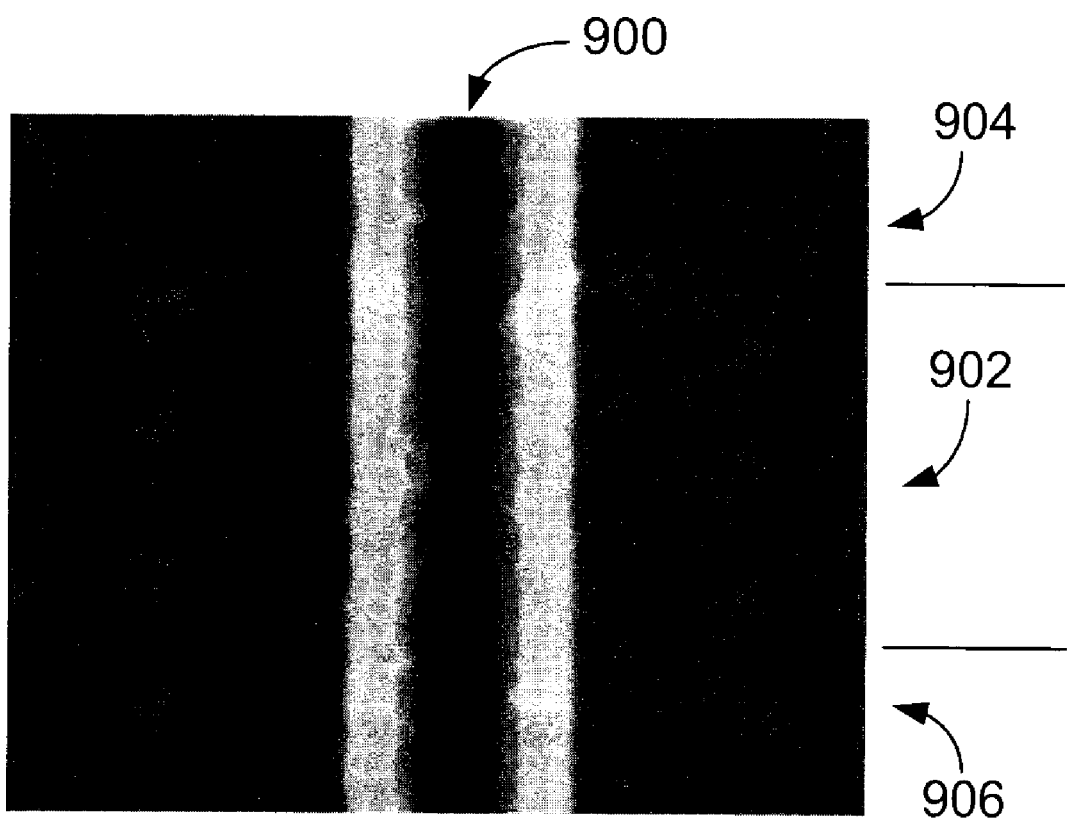
FIG. 9 is an image of a post-etch line pattern produced using a technique for reducing shrinkage carryover due to CD-SEM measurement according to an embodiment.

In comparison, a resist line feature measured with a lower beam voltage (400V) determined using an embodiment of the CD-SEM measurement produced a post-etch line 900 with significantly lower shrinkage carryover (less than 1% of the feature size in P8×5 process), as shown in FIG. 9. In this case, there is little, if any, variation between the average width of the middle section 902 of the etched line 900 compared to the upper section 904 and lower section 906.

A number of embodiments have been described. Nevertheless, it will be understood that various modifications may be made without departing from the spirit and scope of the invention. For example, blocks in the flowcharts may be skipped or performed out of order and still produce desirable results. Accordingly, other embodiments are within the scope of the following claims.

The invention claimed is:

1. A device comprising: a first etched feature, said first etched feature disposed at a measured location, said first etched feature having a shrinkage carryover in a middle section relative to an upper section and a lower section; and a second etched feature, said second etched feature being of the same type as said first etched feature except for being disposed at an unmeasured location, said second etched feature not having said shrinkage carryover in said middle section relative to said upper section and said lower section.

2. The device of claim 1 wherein said upper section, said middle section, and said lower section are completely separated.

3. The device of claim 1 wherein said upper section, said middle section, and said lower section have considerable overlaps.

4. The device of claim 1 wherein said middle section of said first etched feature exhibits a line edge roughness.

5. The device of claim 1 wherein said shrinkage carryover is a physical effect.

6. The device of claim 5 wherein said physical effect is a thermal effect.

7. The device of claim 1 wherein said shrinkage carryover is a chemical effect.

8. The device of claim 7 wherein said chemical effect involves changes in bond structure and atomic group rearrangement.

9. The device of claim 1 wherein said shrinkage carryover is a combination of a physical effect and a chemical effect.

10. The device of claim 1 wherein said shrinkage carryover affects a performance of said device.

11. The device of claim 1 wherein said shrinkage carryover is below a threshold and is tolerable for said device.

12. The device of claim 1 wherein said shrinkage carryover is over a threshold and causes failure or malfunction of said device.

13. The device of claim 1 wherein said shrinkage carryover is not a linear function of feature size.

14. The device of claim 1 wherein said shrinkage carryover is between 10% and 15% for a feature size of 100-200 nm.

15. The device of claim 1 wherein said shrinkage carryover is between 10 nm and 30 nm for a feature size of 100-200 nm.

16. A device comprising an etched feature in an exposure field, said etched feature having an upper section, a middle section, and a lower section wherein said middle section has a shrinkage carryover exceeding a threshold.

17. The device of claim 16 wherein said shrinkage carryover is manifested as a slimming of said middle section.

18. A device comprising a first etched feature disposed in a CD-SEM characterization location, said first etched feature having an upper section, a middle section, and a lower section wherein said middle section is severely shrunk relative to a corresponding middle section of a second etched feature having similar dimensions and composition that is not disposed in a CD-SEM characterization location.

19. The device of claim 18 wherein said middle section of said first etched feature has a shrinkage carryover exceeding a threshold.

20. The device of claim 18 wherein said middle section of said first etched feature exhibits a line edge roughness.

* * * * *